United States Patent [19]

Sebring

[11] Patent Number: 4,761,805
[45] Date of Patent: Aug. 2, 1988

[54] X-RAY RECEPTOR INTERCHANGE MECHANISM

[75] Inventor: John P. Sebring, Townsend, Mass.
[73] Assignee: John K. Grady, Littleton, Mass.
[21] Appl. No.: 931,397
[22] Filed: Nov. 14, 1986
[51] Int. Cl.⁴ .................... G03B 42/04; G03B 42/16
[52] U.S. Cl. .................................. 378/181; 378/167; 378/189; 378/190
[58] Field of Search ............... 378/181, 189, 193, 196, 378/197, 167, 177

[56] References Cited
U.S. PATENT DOCUMENTS
4,358,856  11/1982  Stivender et al. ................. 378/167

Primary Examiner—Carolyn E. Fields
Assistant Examiner—Joseph A. Hynds
Attorney, Agent, or Firm—James H. Grover

[57] ABSTRACT

In medical X-ray apparatus including a stand mounting an X-ray tube and two X-ray receptors such as an image intensifier and a film exchanger, the two X-ray receptors are mounted on a common frame pivoted to present either receptor at the image plane of the X-ray tube. Additionally the two receptors slide on the frame and are linked by a bell crank for coordinated rotation and sliding movement which restores their common center of gravity to its initial locus as one receptor is interchanged for the other. Balance of the receptors with the X-ray tube on the frame is thereby maintained.

15 Claims, 2 Drawing Sheets

X-RAY RECEPTOR INTERCHANGE MECHANISM

BACKGROUND OF THE INVENTION

Originally all x-ray shadowgrams of a human patient were received and recorded on x-ray sensitive film, but it is current medical practice to examine a patient by reception of x-rays on two types of x-ray receptors such as an x-ray image intensifier and film, and modern apparatus must provide for exchanging the positions of the film and intensifier on the x-radiation axis from an x-ray tube. This can be done as shown in U.S. Pat. No. 3,281,598 to Hollstein by retracting the image intensifer and swinging a film holder into the radiation axis in front of the intensifier. Alternatively the film holder may be slid longitudinally into the position vacated by retraction of the image intensifier (Vacher, U.S. Pat. No. 3,614,427; Heitman et al, U.S. Pat. No. 4,298,801). Another method is to rotate an assembly supporting both the film holder and intensifier about the intersection of optical axes of both receptors. A more recent system is to rotate both the image intensifier and film holder jointly 90° and then slide the film holder into the radation axis.

But two major problems arise from the prior methods of interchanging receptors when the receptors are mounted on an x-ray stand with arms for rotation of the x-radiation axis about the patient, and when the film is held, not in a single film plate holder, but in film changer or cassettes which must be over twice as long and twice as thick as each film plate.

The first problem is that a film changer is so thick that, if swung directly into the exposure plane or the x-radiation axis, it will intrude into the zone occupied by the patient risking injury to the patient or disturbance if the patient must be moved.

The second problem is present when the x-ray tube and receptors are mounted on opposite arms of a rotating two-armed support, such as a C- or U-shaped frame. Rotation of the receptors about a point other than their common center of gravity will significantly displace their original center of gravity and destroy the balance of the support arm frame.

It is, of course, necessary to interchange the receptors so that their respective image faces, that is the faces on which the desired x-ray image is formed, move to the same image plane on the radiation axis. But x-ray apparatus in which the receptors are rotated about a point at the intersection of their optical axes so as move their image faces to the same position will necessarily shift their common center of gravity which is not on both optical axes.

Substantially true balance of the rotating frame is important both to safety of the patient under examination and in carrying out of medical routines such as catheterization associated with x-ray examination. If power to the motor rotating the frame should fail, imbalance of the frame could rotate it to a position intruding in the patient zone or preventing ready access to the patient or his life support connections. Imbalance would also prevent delicate manual orientation of the radiation axis by the examining physician and staff as the examination procedure progressed. Adjustment of the rotating frame by hand or by low power, slip clutch motors would be possible if the frame were balanced.

Accordingly it is the object of the present invention to provide a way of interchanging two x-ray receptors at an image plane on the radiation axis while maintaining the balance of rotating arms which support the receptors and the x-ray source.

SUMMARY OF THE INVENTION

According to the invention x-ray apparatus for medical examination of a patient comprises a frame extending to portions at opposite ends of a radiation axis through a patient zone; an x-ray source on one frame portion; and an assembly on the opposite frame portion including first and second x-ray receptors with image faces responsive to x-rays, the receptors having a locus of their combined center of gravity counterbalancing the center of gravity of the x-ray source; characterized in that the frame includes means mounting the respective receptors for rotational and sliding movement of their respective image faces interchangeably to and from a position at the same plane on the radiation axis so as to prevent movement of the radial extremity of either receptor into the patient zone, and a linkage between the receptors controlling their sliding movement so as to locate their combined center of gravity at the counterbalancing locus in either interchange position of the receptors.

DRAWINGS

DESCRIPTION

Figure 1:
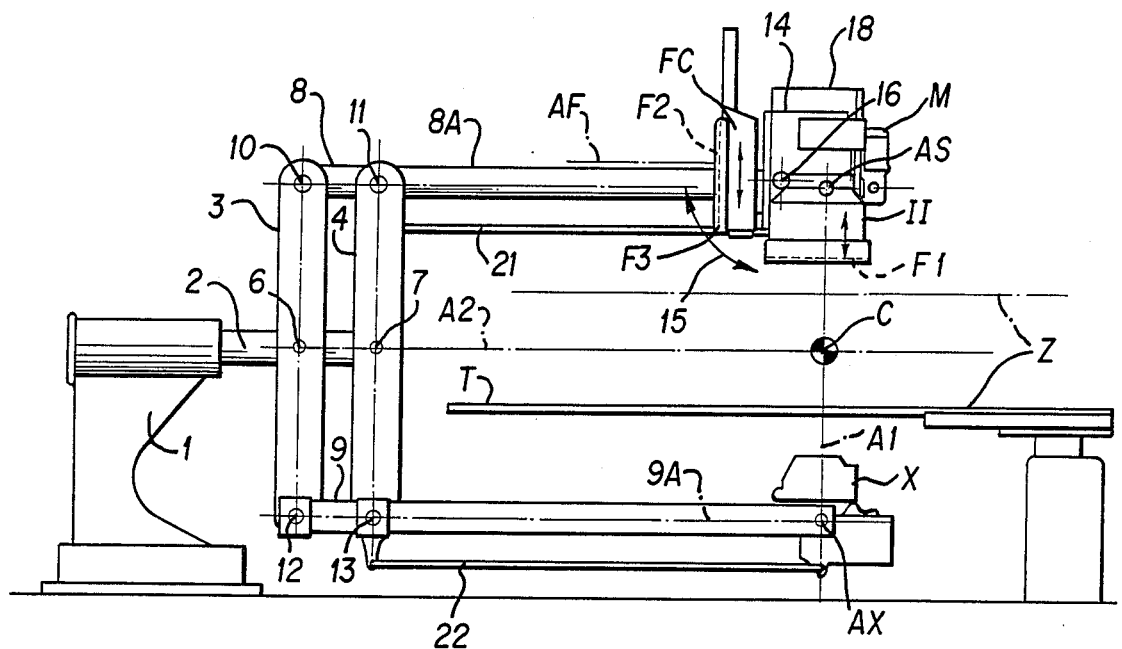
FIG. 1 is a side elevation of x-ray apparatus including an image intensifier and a film changer according to the invention.
Figure 4:
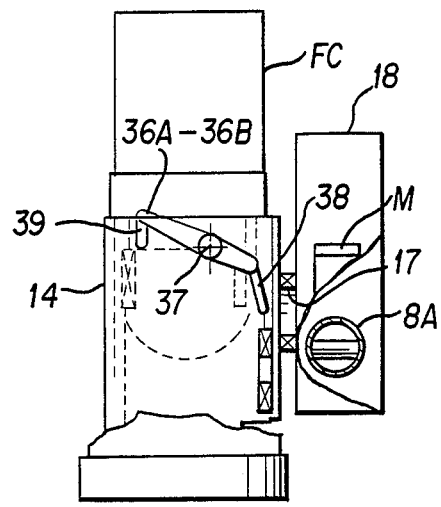
FIG. 4 is a further enlarged end elevation like FIG. 3 with parts broken away.

In the x-ray apparatus of FIG. 1 an x-ray tube X directs a beam of x-rays along a radiation axis A1 to the x-ray responsive face F1 of an x-ray image intensifier II. The radiation axis passes through a zone Z occupied by a patient under examination. The x-ray tube X and image intensifier II are supported on a frame consisting of a standard 1 which may be floor or ceiling mounted, a rotor 2 journalled in the standard for rotation on a horizontal axis A2, two transverse members 3 and 4 centrally pivoted on the rotor 2 at 6 and 7, and upper and lower horizontal arm members 8 and 9 pivotally connected to the transverse members at points 10, 11, 12 and 13 so as to form an adjustable parallelogram as fully described in U.S. Pat. No. 3,892,967. The horizontal members 8 and 9 respectively have extensions 8A and 9A beyond the parallelogram, the x-ray tube X being pivotally supported on a skew axis AX through the lower arm extension 9A. As will be explained in detail the image intensifier II and a film changer FC are mounted on a frame plate 14 which turns about a pivot 16 so as to interchange the positions of the intensifier and changer to and from the radiation axis A1 as indicated by the arcuate, double-headed arrow 15 in FIG. 1. The interchange pivot 16 comprises a rotary bearing 17 mounting the assembly of frame plate, changer FC and intensifier II on a carriage 18, rotating about a skew axis AS through the extension 8A of the upper arm 8 (FIG. 4). Links 21 and 22 between one transverse member and the carriage 18 and x-ray tube X maintain the optical axes of the x-ray tube and intensifier or film changer aligned on the radiation axis A1 through the isocenter C as the parallelogram of the transverse and horizontal members is skewed by rotation about the pivot points 10, 11, 12, 13. The composite angulation by skewing of the radiation axis and rotation about the rotor axis A2 permits examination of a patient from spherical loci equidistant from the isocenter C within a patient.

Figure 2:
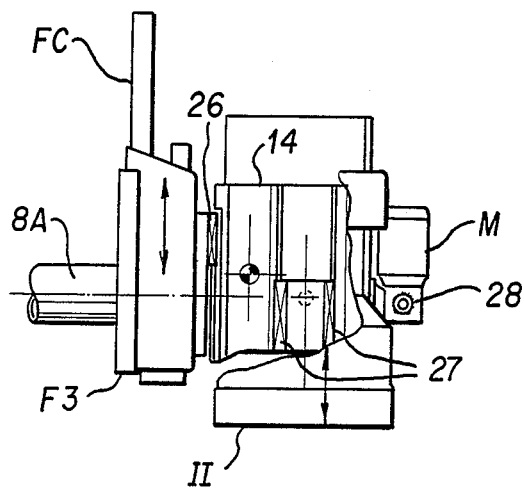
FIG. 2 is an enlarged side elevation of the image intensifier and film changer in FIG. 1.

While the prior x-ray apparatus as so far described operates satisfactorily in general it has two disadvantages. Firstly, if the optical axis AF of the film changer is mounted for simple rotation into coincidence with the radiation axis A1, its radially extreme edge F3 will intrude into the patient zone Z to the hazard or disturbance of the patient. As shown in FIG. 1 this hazard does not exist because the film changer is displaced vertically to a position from which its extreme edge will not swing into the patient zone. However, when in this displaced position as shown in FIGS. 1 and 2, either the film changer optical axis AF will not swing into alignment with the radiation axis A1 because the interchange pivot 16 is not coincident with the film changer axis AF (and the optical axis of the intensifier), or, if these axes and pivot are coincident, the pivot is offset from the combined center of gravity of the film changer and intensifier so that swinging about the pivot shifts the center of gravity of the upper arm 8A and unbalances the system about the rotor axis A2.

Figure 3:
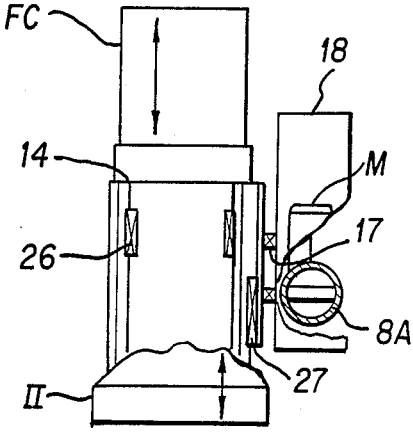
FIG. 3 is an end elevation of the image intensifer and film changer on the same scale as FIG. 2 with parts broken away.

According to the present invention the above disadvantages are avoided by mounting both x-ray receptors, the image intensifier II and film changers, for sliding movement relative to the interchange pivot 16, as indicated by vertical double-headed arrows in FIG. 1. In FIGS. 2 and 3 are shown linear bearings 26 and 27 on which the film changer FC and image intensifier II respectively slide.

Figure 5:
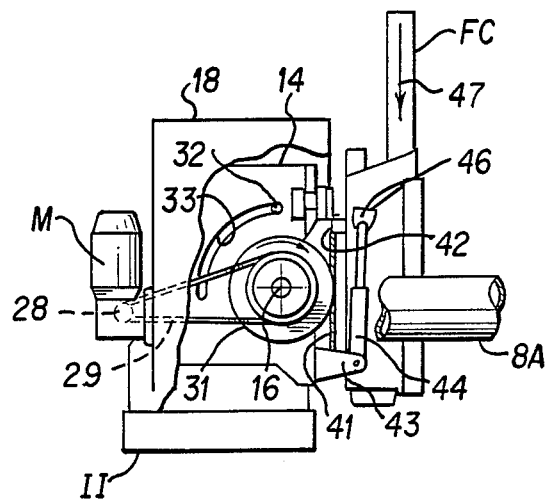
FIG. 5 is an elevation of the image intensifier and film changer at the opposite side from FIG. 2, parts being broken away.

FIGS. 4 and 5 illustrate a drive mechanism for coordinating joint rotational and concomitant sliding movement of the film changer and image intensifier. A motor M mounted on the carriage 18 turns a sprocket wheel 28 coupled by a chain 29 to a pulley or sheave 31 on a shaft set in the carriage 18 on the interchange pivot axis 16 such that rotation of the motor swings the frame plate, changer and intensifier assembly about the interchange axis. A stop 32 set in the carriage 18 slides in a slot 33 concentric with the pivot axis 16 limiting movement of the assembly to ninety degrees, thus swinging the image face F1 of the intensifier out of coincidence with an image plane perpendicular to the radiation axis A1 and swinging the image face F2 of the film changer into the same, vacated image plane but not into a position aligned with the radiation axis. The pulley carries on its periphery a belt 41 anchored at one end 42 to the frame plate and at the other end to a bracket 43 connected by a compression spring 44 pivoted to an anchor 46 on the film changer FC. Rotation of the pulley 31 simultaneously with swinging the frame plate, film changer, intensifier assembly presses the bracket 43 against the spring which resists compression until the stop 32 arrests swinging movement. Further drive from the pulley belt then requires the spring to yield and advances the film changer lengthwise on its linear bearings in the direction of the arrow 47 until its optical axis AF aligns with the radiation axis A1.

As shown in FIG. 4, the film changer FC and image intensifier II are coupled by a bell crank 36A, 36B, pivoted on a stud 37 anchored on the frame plate 14. Links 38 and 39 connect the ends of the bell crank respectively to the film changer FC and image intensifier II. Thus, as the film changer advances lengthwise after the end of its swing, the image intensifier retracts on its linear bearings 27 parallel to the advance of the film changer. The two arms 36A and 36B of the bell crank have lengths inversely proportional to the masses of the film changer and image intensifier respectively. A typical intensifier weighs 160 pounds as against a film changer weight of 130 pounds and the crank arms are proportionally unequal.

Figure 6:
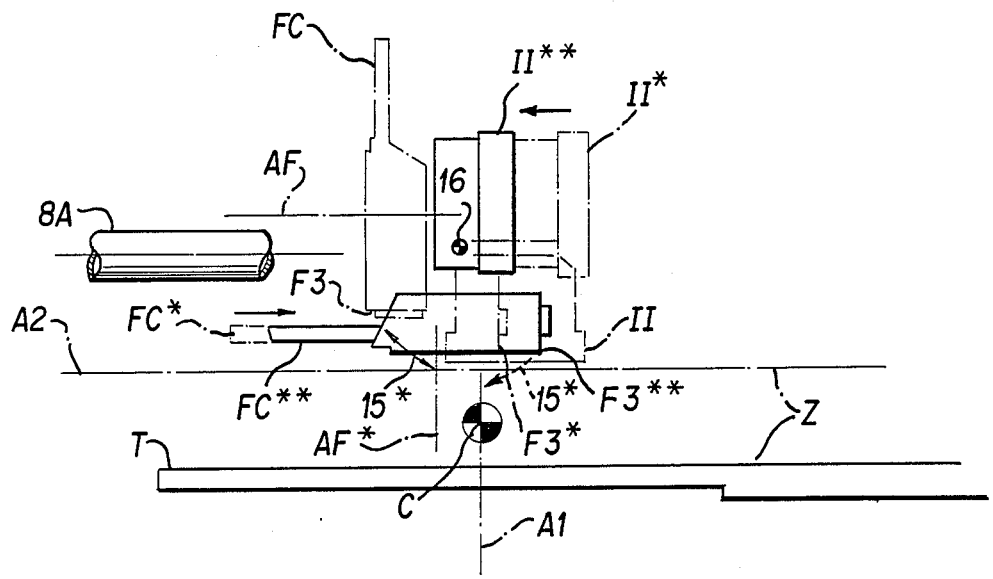
FIG. 6 is a side elevation of a portion of FIG. 1 showing the image intensifer and film changer in interchange positions.

FIG. 6 shows the film changer initial position FC before interchange in dashed outline, its position FC* after rotation in phantom, and in solid line its final position FC** after sliding movement from rotated position. The image intensifier has a corresponding initial dashed line position II, a rotated position II*, and a final position II**. As the image intensifier and film changer rotate about the interchange pivot 16 their combined center of gravity does not shift and upset the balance with the x-ray tube because the interchange pivot is coincident with the combined center of gravity. However, when the film changer has swung to its rotated position FC* its optical axis AF is offset from the radiation axis A1. This offset however prevents the extremity F3 from swinging into the patient zone as indicated by the arrows 15*. The offset of the film changer axis from the radiation axis is thus corrected by sliding the film changer lengthwise to its final interchange position II*, and then slides to its final interchange position II** maintaining the center of gravity in its initial locus. During rotation the spring 44 holds the extremity F3 of the film changer at a radius from the interchange pivot 16 less than the distance from the interchange pivot to the zone Z so as to prevent intrusion of the film changer into the patient zone.

Thus, whereas prior apparatus for interchange of a film changer and an image intensifier or like x-ray receptor destroyed the balance between the x-ray tube and receptor arms and intruded into the patient zone, such hazards are avoided by the present system of concomitant rotation and sliding which also prevents intrusion into the patient zone and effects alignment of the image face of either receptor in the same image plane on the radiation axis, all while maintaining a fixed locus for the center of gravity of the changer and intensifier, and balance of the system about a rotational axis.

It should be understood that the foregoing description is for the purpose of illustration only and this invention includes all modifications and equivalents which fall within the scope of the appended claims.

I claim:

1. X-ray apparatus for medical examination of a patient comprising:
    a frame extending to portions at opposite ends of a radiation axis through a patient zone;
    an x-ray source on one frame portion;
    and an assembly on the opposite frame portion including first and second x-ray receptors with image faces responsive to x-rays, the receptors having a locus of their combined center of gravity counterbalancing the center of gravity of the x-ray source;

characterized in that the frame includes means mounting the respective receptors for rotational movement about an interchange pivot and sliding movement of their respective image faces interchangeably to and from a position at the same plane on the radiation axis so as to prevent movement of the radial extremity of either receptor into the patient zone, and a linkage between the receptors controlling their sliding movement so as to locate their combined center of gravity at the counterbalancing locus in either interchange position of the receptors.

2. Apparatus according to claim 1 wherein the interchange pivot and the center of gravity locus are coincident.

3. Apparatus according to claim 1 wherein each receptor has an optical axis through its image face which is offset from the radiation axis after rotational movement to the plane on the radiation axis, the linkage being proportioned to slide the optical axis into alignment with the radiation axis.

4. Apparatus according to claim 3 wherein the linkage slides the receptors a distance in inverse proportion to their respective masses.

5. Apparatus according to claim 4 wherein the linkage comprises a bell crank with arms extending from a pivot to respective receptors, the length of the arms being inversely proportional to the masses of the receptors.

6. Apparatus according to claim 1 including a motor rotating the receptors between interchange positions.

7. Apparatus according to claim 1 including a motor driving the linkage between the receptors on sliding movement.

8. Apparatus according to claim 7 wherein the motor drives both the rotational and sliding movements of the receptors between interchange positions.

9. Apparatus according to claim 8 wherein linkage includes a spring connected to one receptor so as to yield and delay sliding of the receptor until its rotational movement is arrested.

10. Apparatus according to claim 1 including means to support a patient in a zone adjacent the receptors, wherein the linkage positions one receptor at a radius from the interchange pivot less than the distance from the interchange pivot to the zone so as to prevent intrusion of an extremity of the receptor into the zone.

11. Apparatus according to claim 1 wherein one receptor is an x-ray film changer.

12. Apparatus according to claim 1 wherein one receptor is an x-ray image intensifier.

13. Apparatus according to claim 1 wherein both receptors are slidingly mounted on a common carriage rotatably pivoted on the frame.

14. Apparatus according to claim 1 wherein the frame includes a two-armed support rotating about an axis intersecting the radiation axis to a receptor at an isocenter in the patient zone.

15. Apparatus according to claim 14 wherein the receptor assembly is on one arm and the x-ray source is on the other arm.

* * * * *